United States Patent
Ventura

(10) Patent No.: US 6,302,406 B1
(45) Date of Patent: Oct. 16, 2001

(54) CONNECTOR ASSEMBLY FOR A SURGICAL SAW BLADE

(75) Inventor: Joseph Ventura, Ruckersville, VA (US)

(73) Assignee: Microaire Surgical Instruments, Inc., Charlottesville, VA (US)

( * ) Notice: Subject to any disclaimer, the term of this patent is extended or adjusted under 35 U.S.C. 154(b) by 0 days.

(21) Appl. No.: 09/480,109

(22) Filed: Jan. 10, 2000

(51) Int. Cl.⁷ .............................. B23B 31/20; A61B 17/14
(52) U.S. Cl. .............................. 279/48; 30/392; 30/338; 606/82; 606/177
(58) Field of Search .................. 279/48; 606/82, 606/177; 30/392–394, 336–338, 522

(56) References Cited

U.S. PATENT DOCUMENTS

| | | |
|---|---|---|
| Re. 36,269 | 11/1999 | Wright . |
| 2,282,902 | 5/1942 | Sultan . |
| 2,408,567 | 10/1946 | Mauch . |
| 2,703,716 | 3/1955 | Shore . |
| 3,927,893 | 12/1975 | Dillon et al. . |
| 3,943,934 | 3/1976 | Bent . |
| 3,964,163 | 6/1976 | Russo . |
| 4,020,555 | 5/1977 | Hedrick . |
| 4,036,236 | 7/1977 | Rhodes, Jr. . |
| 4,386,609 | 6/1983 | Mongeon . |
| 4,528,753 | 7/1985 | Kuhlmann et al. . |
| 4,626,146 | 12/1986 | Neumaier . |
| 4,691,929 | 9/1987 | Neumaier et al. . |
| 4,872,452 | 10/1989 | Alexson . |
| 5,306,025 | 4/1994 | Langhoff . |
| 5,340,129 | 8/1994 | Wright . |
| 5,609,603 | * 3/1997 | Linden .................................. 279/75 |
| 5,916,218 | * 6/1999 | Hagen et al. ......................... 606/82 |
| 6,001,115 | * 12/1999 | Ahola et al. ......................... 606/82 |
| 6,209,208 | * 4/2001 | Marinkovich et al. ............... 30/392 |

FOREIGN PATENT DOCUMENTS

| | | |
|---|---|---|
| 4102011A1 | 1/1991 | (DE) . |
| 633103-A1 | * 1/1995 | (EP) ..................................... 279/48 |

* cited by examiner

*Primary Examiner*—Steven C. Bishop
(74) *Attorney, Agent, or Firm*—McGuireWoods LLP

(57) ABSTRACT

A connector assembly for connecting a surgical saw blade to a housing of a surgical instrument. The connector assembly allows a surgeon to align, insert and lock the surgical blade in the collet of the surgical instrument without any special tools, and further provides a stable and robust platform for mounting the surgical saw blade thereto. The connector assembly includes a tapered conical shaped sleeve which is positioned within the housing and rotatable in both a clockwise and counter-clockwise direction. A pair of grippers are mounted within the connector assembly and engage the surgical saw blade when the tapered conical shaped gripper sleeve is rotated in a first position. A sternum guard is also mounted to the housing.

30 Claims, 7 Drawing Sheets

CONNECTOR ASSEMBLY FOR A SURGICAL SAW BLADE

BACKGROUND OF THE INVENTION

1. Field of the Invention

The present invention relates generally to a connector for a surgical saw blade and, more particularly, to a connector assembly for securing a sternum surgical saw blade to a housing of a surgical instrument.

2. Background Description

Collets are an important component of a surgical instrument. In particular, collets are used to mount surgical tools, such as, for example, a surgical saw blade and the like, to a housing of the surgical instrument.

In order to mount and secure a surgical saw blade, for example, within a housing of the surgical instrument it is necessary to place the surgical saw blade into the collet of the surgical instrument. Thereafter, the collet is rotated by a key or a special tool so as to press fit (e.g., friction fit) the surgical saw blade between opposing arms of the collet.

Many of these collets, however, have a tendency to become "stripped" during the mounting of or removal of the surgical saw blade. This poses a severe safety risk to the patient especially if the surgical saw blade breaks or becomes worn and cannot be removed during a surgical procedure. This is simply because the surgeon or other appropriate medical personnel may not be able to remove and replace the surgical saw blade during the surgical procedure. In these cases, the surgical instrument must either be discarded or retrofitted with a new collet.

It is further noted that the surgeon may also strip the key or lose the key which will render the surgical instrument inoperable. Also, using a key during a surgical procedure may be difficult because the surgeon or other medical professional may not be able to properly grip the key in order to open and close the collet, or may drop the key in which case it is not sterile and can no longer be used during the surgical procedure.

A further shortcoming of press or friction fitting the surgical tool within the collet of the surgical instrument is the fact that the surgical instrument can easily become dislodged or loosened during the surgical procedure. This typically happens due to the reciprocating or rotational movement of the surgical tool during the surgical procedure. The loosening or dislodging of the surgical instrument may also be the result of an overused or deteriorated collet, or simply due to the force applied by the surgeon on the surgical instrument during the surgical procedure.

Spring loaded chucking systems used in surgical instruments are also well known in the medical field. However, these spring loaded systems are not robust, and in many instances the tool also becomes loose and/or dislodged. In extreme cases, the tool may even become accidently released from the collet itself, making it very dangerous for both the surgeon and the patient. These spring loaded systems are also designed in such a manner that the surgeon may accidently "hit" the spring loaded release mechanism during use thereof. In this case, the tool can spontaneously eject from the surgical instrument posing serious injury to both the surgeon and the patient.

What is thus needed is a connector assembly that is easy to use and which securely mounts and locks the surgical tool within the housing of the surgical instrument. Such an assembly would also provide safety features to protect the surgeon and the patient, and would preferably be a keyless system. This assembly would afford a stable platform for the surgical tool.

SUMMARY OF THE INVENTION

It is therefore an object of the present invention to provide a connector assembly which securely mounts and locks a surgical saw blade within a collet of a surgical instrument.

It is also an object of the present invention to provide a connector assembly which properly aligns a surgical saw blade within the housing of the surgical instrument prior to locking the surgical saw blade to the collet.

It is a further object of the present invention to provide a surgical connector assembly which locks the surgical saw blade within the collet of the surgical instrument without any special tools, equipment and the like.

It is also a further object of the present invention to provide a connector assembly which allows a surgeon to easily remove and replace the surgical saw blade during a surgical procedure.

It is still a further object of the present invention to provide a connector assembly which ensures that a sternum guard is properly mounted and locked to the housing of the surgical instrument.

It is yet another object of the present invention to provide a connector assembly which allows the sternum guard to be mounted to the collet of the surgical instrument only after the surgical saw blade is properly mounted within the housing of the surgical instrument.

According to the invention, there is provided a connector assembly for connecting a surgical saw blade to a collet of a surgical instrument. The connector assembly allows a surgeon to align, insert and lock the surgical blade in the collet of the surgical instrument without any special tools, equipment and the like. This enables the surgeon or other medical personnel to easily remove and replace the surgical saw blade during a surgical procedure, and further provides a stable and robust platform for mounting the surgical saw blade thereto. Also, the connector assembly of the present invention provides an added safety feature by ensuring that a sternum guard is properly mounted to the housing of the surgical instrument only after the surgical saw blade is completely inserted and secured within the connector assembly of the present invention.

More particularly, the present invention includes a connector assembly which attaches a surgical saw blade to a collet of a surgical instrument. The connector assembly includes a finger gripper sleeve which is positioned within the housing. The finger gripper sleeve includes a tapered conical end portion and an inner threaded portion. The inner threaded portion is in threaded communication with a threaded sleeve mounted to the housing. This threaded communication allows the finger gripper sleeve to be rotated in both a clockwise and counter-clock wise direction.

A collet holder is positioned within the housing and includes two outwardly extending arms. A collet is positioned between the outwardly extending arms of the collet holder and includes a slot for accommodating the surgical saw blade when the surgical saw blade is positioned and securely mounted within the connector assembly. A shoulder portion of the threaded sleeve fits over the collet holder.

The connector assembly further includes a pair of outwardly biased springs or other elastic members. A pair of grippers are mounted on an end of each of the outwardly biased springs respectively such that the grippers are biased outwardly by the outwardly biased springs. Each of the grippers include a downwardly extending projection and an outer conical radial surface which corresponds to the tapered conical portion of the finger gripper sleeve. The grippers are aligned with the slot of the collet.

In order to insert and lock the surgical saw blade into the connector assembly, the surgical saw blade is first aligned and inserted into the slot of the collet. By having this proper alignment, engagement portions on opposing side edges of the surgical saw blade will self-align with the downwardly extending projections of the grippers. To properly secure the surgical saw blade to the connector assembly, the inner threaded portion of the finger gripper sleeve is then rotated in the clockwise direction until the pair of grippers are biased or "squeeze" toward the center of the housing and engaged with the engagement portions of the surgical saw blade.

The sternum guard is mounted to the housing after the finger gripper sleeve is fully rotated in the closed or secured position. When the finger gripper sleeve is in the closed position, a clearance "Δ" is created between the sternum guard and the end of the gripper sleeve. This clearance "Δ" permits enough space for the sternum guard to be properly mounted to the housing.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF THE PREFERRED EMBODIMENT OF THE INVENTION

The present invention is directed to a connector assembly for connecting a surgical saw blade to a housing of a surgical instrument. The connector assembly is a keyless system and is capable of connecting several types of surgical saw blades including, for example, a sternum surgical saw blade, to the housing of the surgical instrument. By using the connector assembly of the present invention, a surgeon or other medical personnel can easily align, insert and lock the surgical blade in the collet of the surgical instrument without any special tools, equipment and the like. This enables the surgeon or other medical personnel to easily remove and replace the surgical saw blade during a surgical procedure. The connector assembly of the present invention also provides a stable and robust platform for mounting of the surgical saw blade Also, by using the connector assembly of the present invention, a sternum guard can also be mounted to the housing of the surgical instrument after the surgical saw blade is completely inserted and secured within the connector assembly of the present invention. This provides an added safety feature to both the surgeon and the patient. It is further noted that the sternum guard may also be mounted and removed from the surgical instrument without the use of any special tools and the like.

Figure 1:
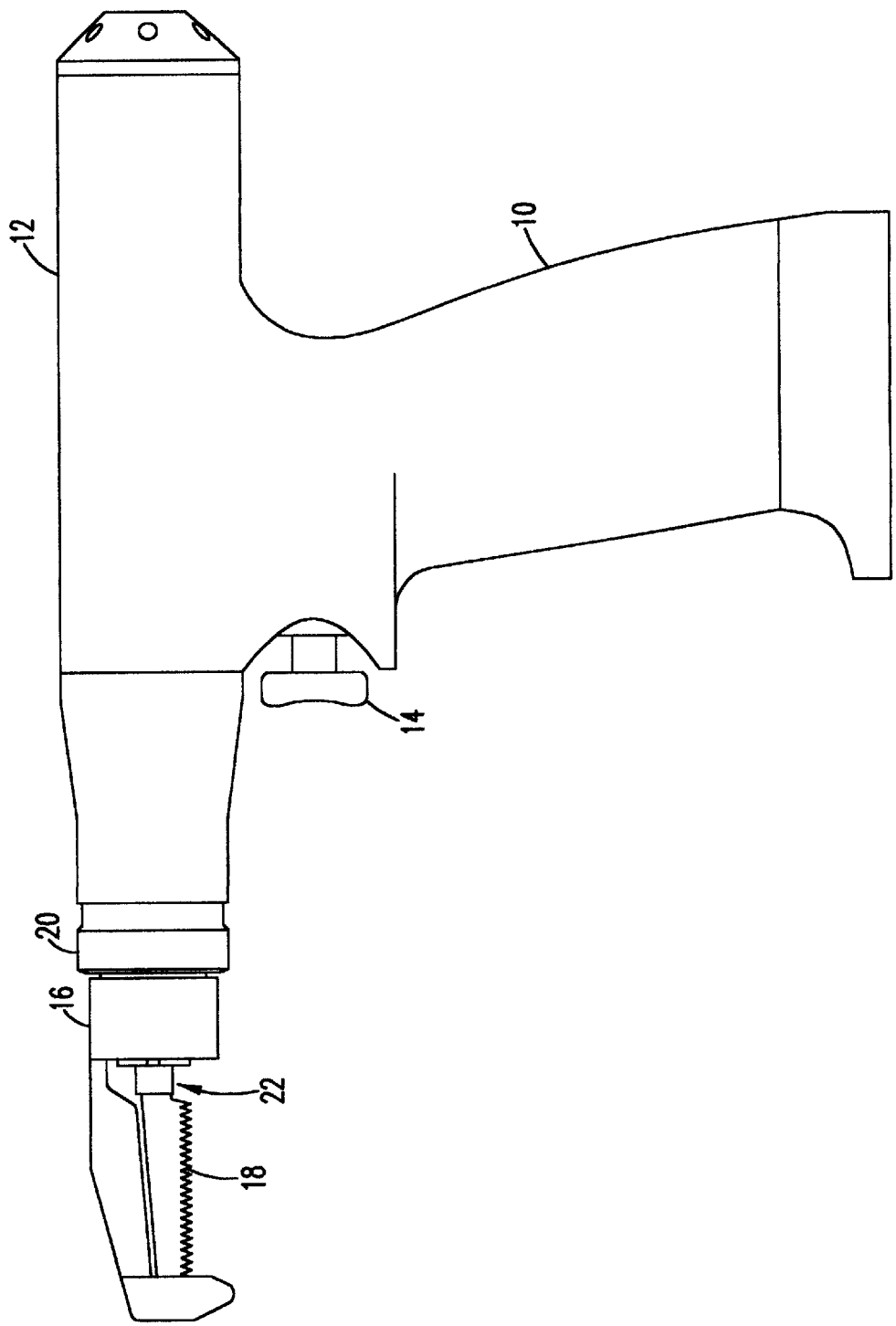
FIG. 1 shows a plan view of a surgical saw using a connector of the present invention.

Referring now to the drawings, and more particularly to FIG. 1, there is shown a plan view of a surgical saw using a connector assembly of the present invention. More particularly, the surgical saw includes a pistol type grip 10 connected to a housing 12. The housing 12 houses the connector assembly 22 of the present invention (as described with reference to FIGS. 2–4) as well as a reciprocating drive mechanism. In the preferred embodiment, an electric motor drives the drive assembly and is driven by a 14V power supply. It should be well understood that the pistol type grip 10 and the housing 12 are not critical to the understanding of the present invention and are provided herein only for illustration. For example, a wand type handle or other configuration can equally be used with the present invention.

A trigger 14 is coupled to the pistol type grip 10 and is used to adjustably control the speed of the drive mechanism between a maximum speed and an "off" position. Speed controls other than the trigger 14 may also be used with the present invention without departing from the scope of the present invention. These speed controls may be, for example, separate speed control buttons.

Still referring to FIG. 1, a connector assembly 22 attaches the surgical saw blade 18 to the collet of the housing 12. A sternum guard 16 is also mounted to the end of the housing 12 and extends the length of the surgical saw blade 18 so as to protect a patient from being inadvertently injured by the reciprocating movement of the surgical saw blade 18 during a surgical procedure. A finger release button 20 communicates with the sternum guard 16 and locks the sternum guard 16 to the housing 12. The sternum guard 16 may be removed from the housing 12 when the finger release button 20 is depressed by a surgeon or other user of the surgical saw. It is noted that the present invention is not limited to the finger release button 20 and that other selectively actuatable members may be used to lock the sternum guard 16 to the housing 12 in order to safely retain the sternum guard 16 on the housing 12.

Figure 2:
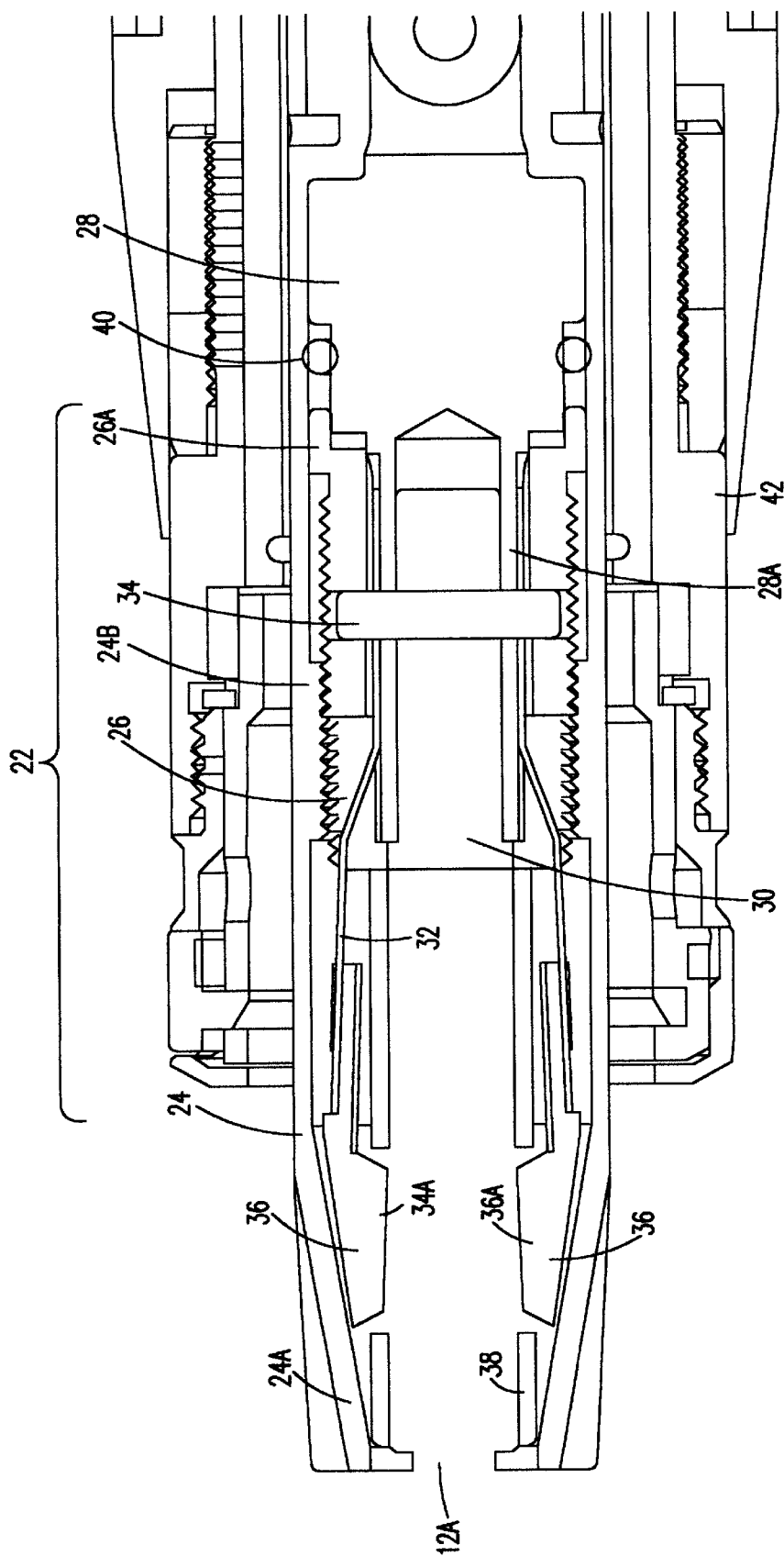
FIG. 2 shows a side cutaway view of the connector assembly of the present invention.

FIG. 2 shows a side cutaway view of the connector assembly 22 of the present invention. Specifically, the connector assembly 22 of the present invention includes a finger gripper sleeve 24 which is positioned within the housing 12. The finger gripper sleeve 24 includes a tapered conical end portion 24a and an inner threaded portion 24b. The inner threaded portion 24b is in threaded communication with a threaded sleeve 26 which is securely mounted to the housing 12.

The threaded communication between the inner threaded portion 24b of the finger gripper sleeve 24 and the threaded sleeve 26 allows the finger gripper sleeve 24 to be rotated in both a clockwise and counter-clock wise direction. In the embodiment shown in FIG. 2, the finger gripper sleeve 24 is in a first position or open position. It is noted that the finger gripper sleeve 24 may be positioned in a second position or close position when the finger gripper sleeve 24 is rotated in the clockwise direction, or may be partly removed from the housing 12 when the finger gripper sleeve 24 is sufficiently rotated in the counter-clockwise direction. The finger gripper sleeve 24 cannot preferably be removed from the housing due to the pins 24 pressed in the finger gripper sleeve 24.

Still referring to FIG. 2, a collet holder 28 is positioned within the housing 12 (and finger gripper sleeve 24) and includes two outwardly extending arms 28a. In the embodiment of the present invention, the collet holder 28 may include an outwardly extending collar or similar structure (instead of the arms 28a), and may further include an O-ring 40 placed between the collet holder 28 and an inner surface of the finger gripper sleeve 24. The O-ring 40 may provide a predetermined amount of tension between the collet holder 28 and the finger gripper sleeve 24 so as to securely hold the finger gripper sleeve 24 in a properly aligned position. A collet 30 is positioned between the outwardly extending arms 28a (and preferably between two springs as discussed below) of the collet holder 28 and includes a slot for accommodating the surgical saw blade 18 when the surgical saw blade 18 is positioned and securely mounted within the connector assembly 22. The width of the slot is substantially equal to the thickness of the surgical saw blade 18. A shoulder portion 26a of the threaded sleeve 26 is mounted on the collet holder 28.

The connector assembly 22 of the present invention further includes a pair of outwardly biased springs 32 (or other similar elastic member). A first end of each of the outwardly biased springs 32 is positioned proximate to "knocks" of a collet 30 and is further positioned within an inner portion of the threaded sleeve 26. In the preferred embodiment, a pin 34 securely locks together the assembly comprising (i) the collet holder 28, (ii) each of the outwardly biased springs 32, (iii) the collet 30 and (iv) the threaded sleeve 26.

FIG. 2 further shows two grippers 36 positioned at a second end of each of the outwardly biased springs 32, respectively. The grippers 36 are biased outwardly (e.g., toward the surface of the collet 30) by the outwardly biased springs 32. Each of the grippers 32 include a downwardly extending projection 36a and an outer conical radial surface. The downwardly extending projection 36a may include a rounded end which corresponds to a rounded portion of a hub of a type of saw blade hub (FIG. 4), and the outer conical radial surfaces correspond to the tapered conical portion 24a of the finger gripper sleeve 24. The grippers 36 should be preferably aligned with the "knocks" (e.g., slots) of the collet 30 so that the surgical saw blade 18 can be securely mounted to the connector assembly 22 as discussed in detail below. In an embodiment of the present invention, a single gripper 36 may only be required in order to practice the present invention.

As seen further in FIG. 2 and discussed in greater detail with reference to FIG. 10, an end sleeve 38 is fitted within the housing 12 proximate to the open end 12a of the housing 12. The end sleeve 38 includes a pair of windows which are in alignment with the downwardly extending projections 36a. The downwardly extending projections 36a pass through the windows when the surgical saw blade 18 is mounted to the connector assembly 22 (as discussed with reference to FIGS. 3 and 4).

Figure 3:
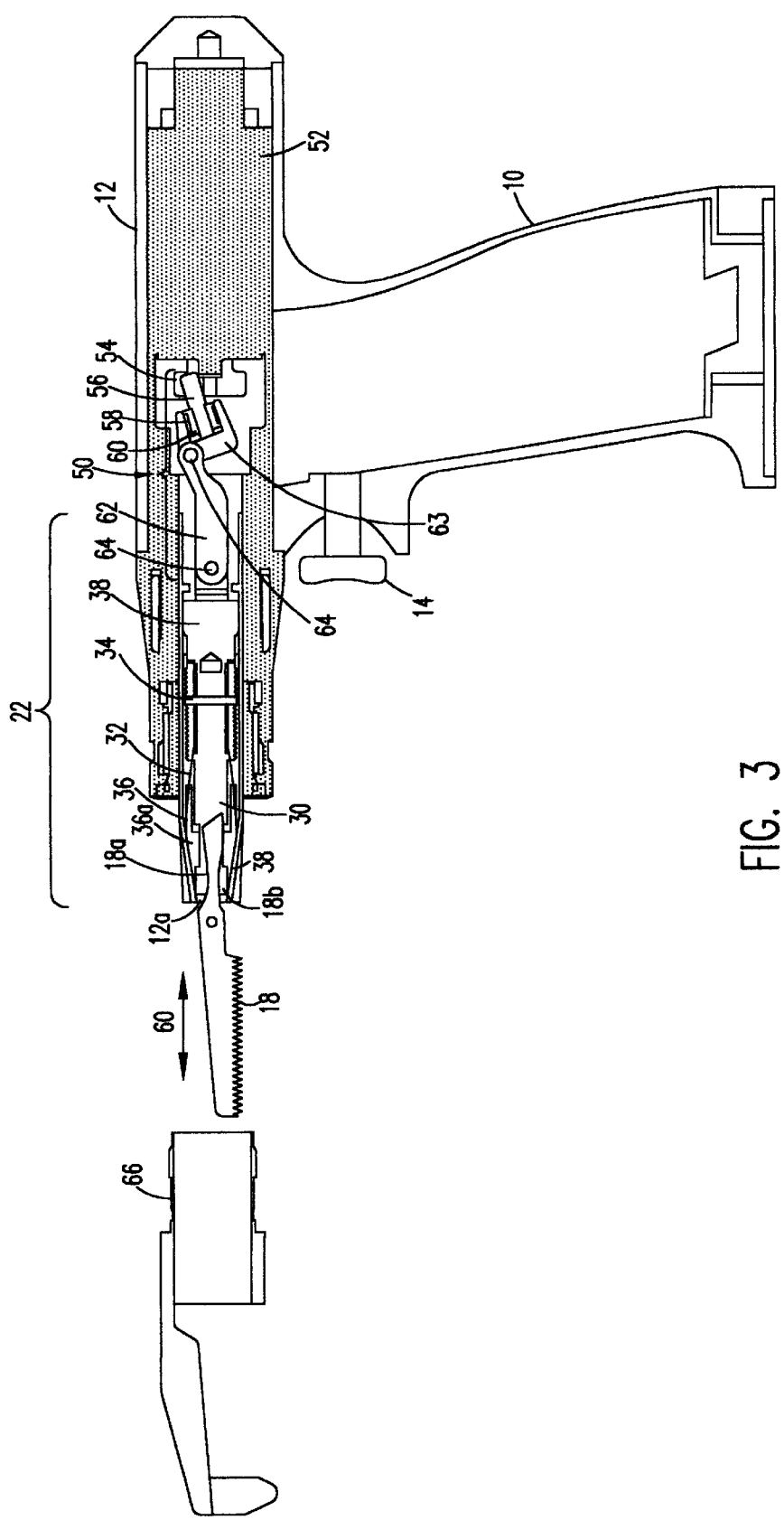
FIG. 3 shows a distal end of the surgical saw blade partially inserted within the connector assembly of the present invention.

FIG. 3 shows a distal end 18a of the surgical saw blade 18 partially inserted within the connector assembly 22 of the present invention. In this stage of insertion of the surgical saw blade 18 into the connector assembly 22, the finger gripper sleeve 24 is in a substantially or completely open position. In this position, the grippers 36 are not biased toward the center of the collet 30 and thus do not engage the surgical saw blade 18. In other words, the grippers 36 remain outwardly biased by the outwardly biased springs 32 so that the surgical saw blade 18 can be inserted within the end 12a of the housing 12 and partially within the connector assembly 22. It is noted that the finger gripper sleeve 24 does not have to be completely in the open position for the surgical saw blade 18 to be inserted therein; however, it is critical to the understanding of the present invention that the finger gripper sleeve 24 must be in such a position to allow the grippers 36 to remain biased outwardly (at a predetermined distance) so that the surgical saw blade 18 can be inserted therethrough.

FIG. 3 also shows the drive mechanism 50 of the surgical saw. This drive mechanism 50 is a conventional mechanism and is discussed herein for clarity purposes only. Specifically, a motor 52 is coupled to a driver 54 which, in turn, is coupled to an eccentric pin 56. The eccentric pin 56 is coupled to a claw 63 by a barrel 60 and bushing 58. A collet driver arm 62 is coupled between the collet holder 38 and the claw 63 via pins 64. As should be readily apparent to one of ordinary skill in the art, the rotational movement of the motor 52 is translated into a reciprocating movement via the drive mechanism 50. This reciprocating movement is then translated to the surgical saw blade 18 via the collet assembly so that the surgical saw blade 18 can reciprocate in the directions shown by arrow 60. It should further be well understood by one of ordinary skill in the art that the drive mechanism shown in FIG. 3 is presented herein for illustrative purposes only, and that other drive mechanisms for providing a reciprocating movement to the surgical saw blade 18 can equally be used with the present invention.

Figure 4:
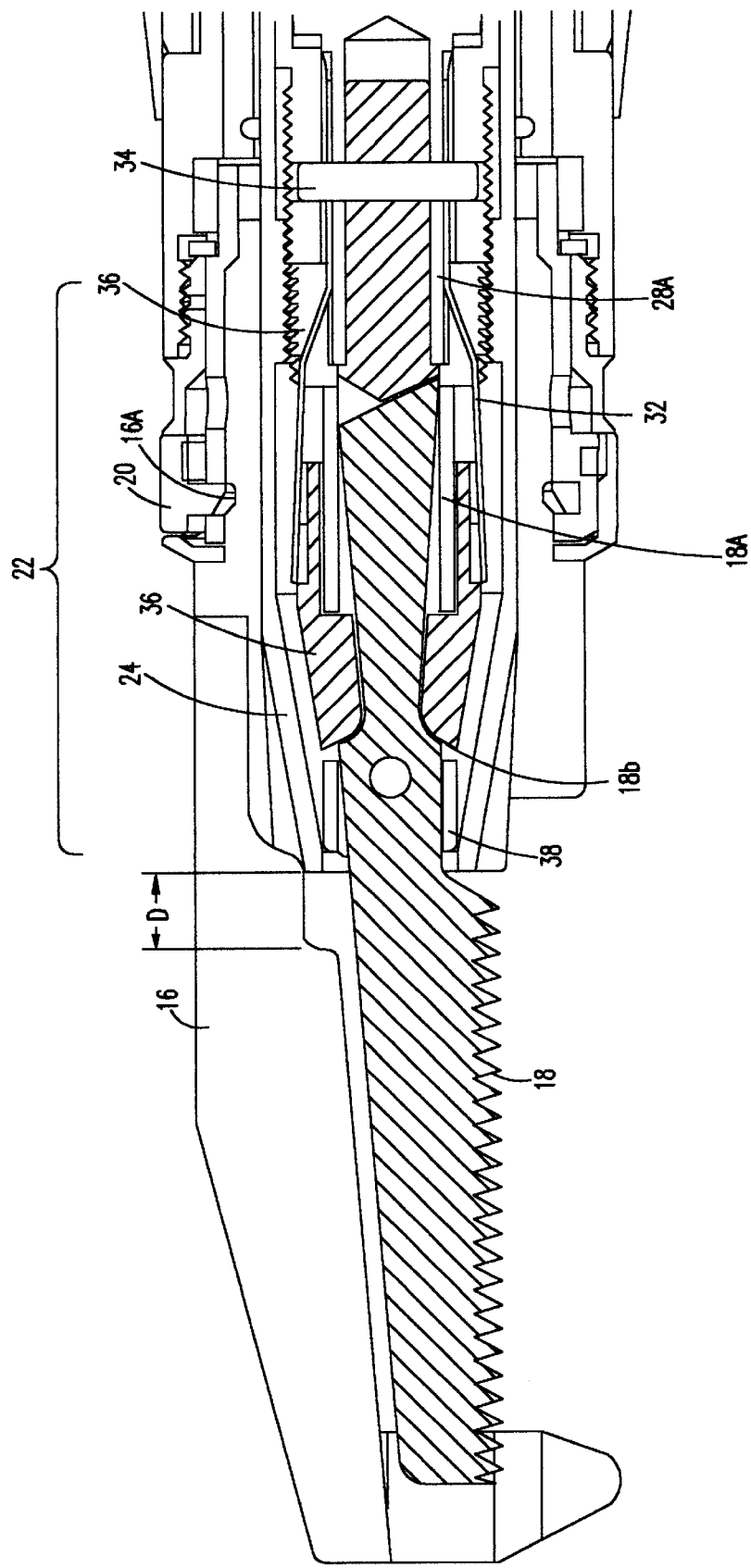
FIG. 4 shows the surgical saw blade inserted and locked within the connector assembly of the present invention.

FIG. 4 shows the surgical saw blade 18 completely inserted and locked within the connector assembly 22 of the present invention. In order to properly insert the surgical saw blade 18 into the connector assembly 22, the surgical saw blade 18 is first inserted through the sleeve 38 and then aligned with the slot of the collet 30. Once properly aligned with the slot of the collet 30, the surgical saw blade 18 may then be fully inserted into the connector assembly 22. By having this proper alignment, engagement portions 18b on opposing side edges of the surgical saw blade 18 will self-align with the downwardly extending projections 36a of the grippers 36. At this stage, the finger gripper sleeve 24 is in the substantially or completely open position as described with reference to FIG. 3.

To properly secure the surgical saw blade 18 to the connector assembly 22, the inner threaded portion 24b of the finger gripper sleeve 24 is then rotated in the clockwise direction until the tapered conical portion 24a of the finger gripper sleeve 24 contacts the outer conical radial surface of the pair of grippers 36. As the finger gripper sleeve 24 is further rotated in the clockwise direction, the outer conical radial surface of the pair of grippers 36 slides along the narrowed tapered conical portion 24a of the finger gripper sleeve 24 and are biased or "squeeze" through the windows of the end sleeve 28 (toward the center of the collet 30). Once the finger gripper sleeve 24 is further rotated in the clockwise direction, the grippers 36 are further inwardly biased and begin to engage the engagement portions 18b of the surgical saw blade 18. At a predetermined point in the rotation of the finger gripper sleeve 24, the grippers 36 completely engage the engagement portions 18b of the surgical saw blade 18 to secure the surgical saw blade 18 to the collet 30. This predetermined position may be any desirable position, and may depend on such factors as the length of the blade portion of the surgical saw blade 18, the size of the finger gripper sleeve 24 and the like.

As seen further in FIG. 4, the sternum guard 16 is also mounted to the housing 12. As a safety feature and in the preferred embodiment, the sternum guard 16 may only be mounted to the housing 12 after the surgical saw blade 18 is fully mounted and locked onto the connector assembly 22. That is, the sternum guard 16 may be mounted to-the housing 12 only after the finger gripper sleeve 24 is rotated in the clockwise direction to a substantially closed position.

More specifically and referring now to both FIG. 3 and FIG. 4, when the finger gripper sleeve 24 is in the open position (FIG. 3), the finger gripper sleeve 24 substantially extends beyond an end of the housing 12. This extended portion of the finger gripper sleeve 24 interferes with a portion of the sternum guard 16 and prevents the sternum guard 16 from being properly mounted to the housing 12. However and as seen in FIG. 4, when the finger gripper sleeve 24 is rotated in the clockwise direction to the closed position it no longer extends substantially from the end of the housing 12 thus allowing the sternum guard 16 to be mounted on the housing 12. That is, the interference between the finger gripper sleeve 24 and the sternum guard 16 will no longer exist when the finger gripper sleeve 24 is rotated in the clockwise direction to the closed position. In fact, as seen in FIG. 4, a clearance "Δ" is created between the sternum guard 16 and the end of the gripper sleeve 24 when the finger gripper sleeve 24 is rotated in the clockwise direction to the closed position. This clearance "Δ" permits enough space for the sternum guard 16 to be properly mounted to the housing 12. Once mounted to the housing 12, the finger release button 20 engages a notch 16a on the sternum guard 16 in order to lock the sternum guard 16 to the housing 12. The sternum guard 16 may be removed from the housing 12 when the finger release button 20 is depressed by a surgeon or other user of the surgical saw.

Figure 5:
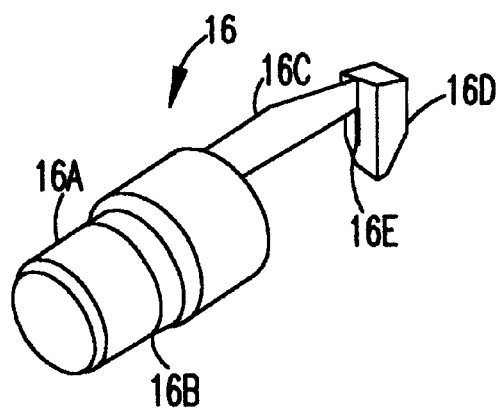
FIG. 5 shows a plan view of a sternum guard.

FIGS. 5–10 show the specific components of the connector assembly of the present invention. Referring now to FIG. 5, a plan view of the sternum guard 16 is shown. The sternum guard 16 includes a guard collar 16b which is mounted to the housing 12 and the notch 16a which is engaged by the finger release button 20. An outwardly extending arm 16c extends from the sternum guard collar 16b and connects to a guide guard 16d. The outwardly extending arm 16c should preferably be substantially the same length as the blade portion of the surgical saw blade 18. A slot 16e is located within the guide guard 16d so that the surgical saw blade 18 can reciprocate therethrough. In the preferred embodiment, the surgical saw blade 18 will not extend through the entire slot 16e during the reciprocating movement of the surgical saw blade 18. This ensures that the end of the surgical saw blade 18 will not inadvertently injure a patient during a surgical procedure.

Figure 6:
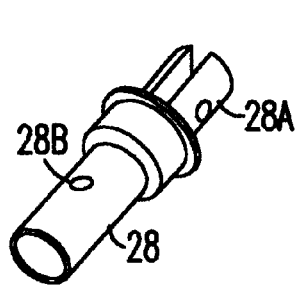
FIG. 6 shows a plan view of a collet holder.

FIG. 6 shows a plan view of a collet holder 28. The collet holder 28 includes the two outwardly extending arms 28a and a bore 28b within the body of the collet holder 28. The bore 28b allows the pin 34 to pass therethrough so that the collet holder 28 can be locked to each of the outwardly biased springs 32, the collet 30 and the threaded sleeve 26.

Figure 7:
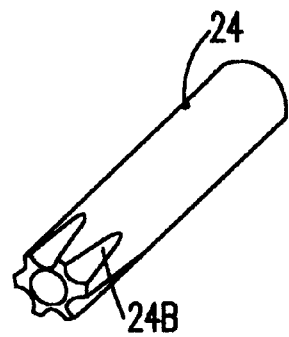
FIG. 7 shows a plan view of a finger gripper sleeve.

FIG. 7 shows a plan view of the finger gripper sleeve 24. As seen in FIG. 7, the finger gripper sleeve 24 includes a milled or machined end portion 24 which enables the surgeon or other medical personnel to easily grip the finger gripper sleeve 24. This allows the surgeon or other medical personnel to rotate the finger gripper sleeve 24 in either the clockwise or counter-clockwise direction without the use of any tools or other special equipment. Although a "hex" configuration is shown in FIG. 7, other machined patterns or configurations are contemplated for use by the present invention, such as, for example, rectangular, square, pentagonal and the like.

Figure 8:
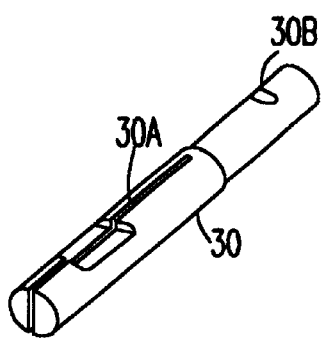
FIG. 8 shows a plan view of a collet.

FIG. 8 shows a plan view of the collet 30. The collet 30 includes a slot 30a for accommodating the surgical saw blade 18 when the surgical saw blade 18 is positioned within the connector assembly 22. The slot 30a also allows the engagement portions 18b of the surgical saw blade 18 to self-align with the downwardly extending projections 36a of the grippers 36. The collet 30 also includes a bore 30b which allows the pin 34 to pass therethrough so that the collet 30 can be locked or pinned to the collet holder 28, outwardly biased springs 32 and the threaded sleeve 26.

Figure 9:
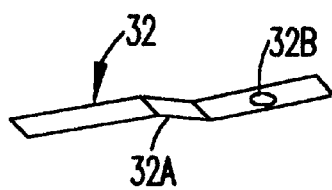
FIG. 9 shows a plan view of an elastic member.

FIG. 9 shows a plan view of one of the outwardly biased springs 32 (or other similar elastic member). The outwardly biased springs 32 include a stepped portion 32a and a bore 32b. A distal end of the stepped portion 32a is connected to the gripper 36 (FIG. 2), and provides for the necessary clearance between the finger grippers 36 and the engagement portion 18b of the surgical saw blade 18 when the surgical saw blade 18 is first inserted into the connector assembly 22. The bore 30b allows the pin 34 to pass therethrough so that the outwardly biased springs 32 can be locked to each of the grooves of the collet holder 28, the collet 30 and the threaded sleeve 26.

Figure 10:
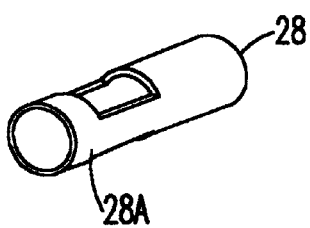
FIG. 10 shows a plan view of an end sleeve.

FIG. 10 shows a plan view of the end sleeve 28. The end sleeve 28 includes windows 28a which are aligned with the downwardly extending projections 36a. The windows 28a of the end sleeve 28 permit the downwardly extending projections 36a to communicate with the surgical saw blade 18 when the finger gripper sleeve 24 is rotated to the closed position.

Figure 11:
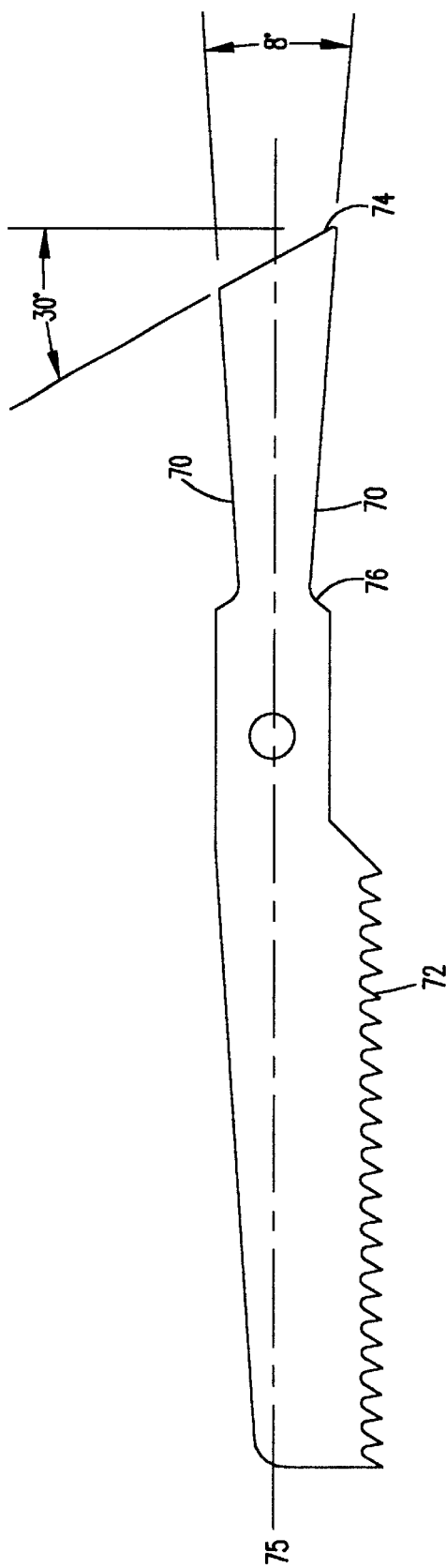
FIG. 11 shows a plan view of the surgical saw blade.

FIG. 11 shows a plan view of the surgical saw blade. The surgical saw blade includes opposing sloped surfaces 70 extending substantially from a blade portion (teeth) 72 to an end 74 of the saw blade. Preferably, the opposing sloped surfaces 70 extend outward with relation to a lateral axis 75 of the saw blade. The surgical saw blade further includes substantially semi-rounded inner surfaces 76 at an interface between the opposing sloped surfaces 70 and the saw blade 72. The end 74 of the saw blade preferably has a slope end of approximately 30 degrees. When the surgical saw blade is installed into the collet system of the present invention, the rounded ends of the downwardly extending projection 36a correspond to the semi-rounded inner surfaces 76 of saw blade hub (FIG. 4). The remaining portion of the of the downwardly extending projection 36a engage the opposing sloped surfaces 70 of the surgical saw blade. These features provide a positive locking system.

While the invention has been described in terms of its preferred embodiments, those skilled in the art will recognize that the invention can be practiced with modification within the spirit and scope of the appended claims.

Having thus described my invention, what I claim as new and desire to secure by Letters Patent is as follows:

1. A connector assembly for connecting a surgical saw blade to a housing of a surgical instrument, the connector assembly comprising:

a tapered gripper sleeve connected to the housing, the tapered gripper sleeve being adapted to move between a first position and a second position; and a gripper mechanism positioned with the tapered gripper sleeve, the gripper mechanism having at least one extending projection moveable with respect to the tapered gripper sleeve and adapted to engage a engagement portion on a side edge of the surgical saw blade when the tapered gripper sleeve is in the first position.

2. The connector assembly of claim 1, wherein the tapered gripper sleeve includes a tapered conical end portion and an inner threaded portion, the at least one extending projection being inwardly biased by the tapered conical end portion when the tapered gripper sleeve is in the first position.

3. The connector assembly of claim 2, further comprising a threaded sleeve mounted to the housing, wherein the inner threaded portion of the tapered gripper sleeve is in threaded communication with threaded sleeve.

4. The connector assembly of claim 3, wherein
   the tapered gripper sleeve is rotated between the first position and the second position about the threaded sleeve, and
   the at least one extending projection contacts the tapered conical end portion when the tapered gripper sleeve is rotated in substantially the first position such that the at least one extending projection is biased inwardly to thereby engage the engagement portion of the surgical saw blade.

5. The connector assembly of claim 1, further comprising a collet holder positioned within the housing and proximate to a first end of the tapered gripper sleeve.

6. The connector assembly of claim 5, wherein the collet holder includes one of two outwardly extending springs and an outwardly extending collar.

7. The connector assembly of claim 5, further comprising means for connecting the collet holder to the tapered gripper sleeve.

8. The connector assembly of claim 5, further comprising a collet being positioned between the outwardly extending arms of the collet holder, the collet including a slot adapted to accommodate the surgical saw blade.

9. The connector assembly of claim of claim 8, wherein the slot is in alignment with the at least one extending projection of the gripper mechanism.

10. The connector assembly of claim of claim 1, further comprising means for outwardly biasing the at least one extending projection when the tapered gripper sleeve is in the second position.

11. The connector assembly of claim of claim 10, wherein the means for outwardly biasing the at least one extending projection includes at least one of a spring and an elastic member.

12. The connector assembly of claim 1, wherein the at least one extending projection is two opposing extending projections.

13. The connector assembly of claim 1, wherein the gripper mechanism includes an outer surface which corresponds to a slope of the tapered gripper sleeve.

14. The connector assembly of claim 1, further comprising an end sleeve, the end sleeve including at least one window corresponding to a position of the at least one extending projection, the at least one extending projection extending through the at least one window when the at least one extending projection engages the engagement portion on the surgical saw blade.

15. The connector assembly of claim 1, wherein the tapered gripper sleeve extends from the housing and includes a machined end portion adapted for a surgeon to grip the tapered gripper sleeve.

16. The connector assembly of claim 15, wherein the machined end portion is shaped as a hexagon, rectangle, square or pentagon.

17. A surgical instrument comprising:
   a housing;
   a motor and drive assembly being housed within the housing;
   a tapered sleeve being coupled to the housing and proximate to the motor and drive assembly, the tapered sleeve being adapted to move between a first position and a second position;
   a gripper mechanism positioned with the tapered sleeve, the gripper mechanism having projection means moveable with respect to the tapered sleeve and adapted to engage a side edge of the surgical saw blade when the tapered sleeve is in the first position; and
   a sternum guard mounted to an end of the housing and proximate to the surgical saw blade.

18. The surgical instrument of claim 17, wherein the sternum guard includes a guard collar mounted to the housing and an outwardly extending arm which extends from the sternum guard collar and along a length of the surgical saw blade.

19. The surgical instrument of claim 18, further comprising:
   a selectively actuatable member positioned on the housing; and
   a notch positioned on the guard collar of the sternum guard,
   wherein the selectively actuatable member engages the notch when the guard collar is mounted to the housing.

20. The connector assembly of claim 19, wherein the tapered sleeve includes a tapered conical end portion and an inner threaded portion, the projection means being inwardly biased by the tapered conical end portion when the tapered sleeve is in the first position.

21. The connector assembly of claim 19, further comprising a threaded sleeve mounted to the housing,
   wherein the inner threaded portion of the tapered sleeve is in threaded communication with threaded sleeve,
   wherein the tapered sleeve is rotated between the first position and the second position about the threaded sleeve, and
   wherein the projection means contacts the tapered conical end portion when the tapered sleeve is rotated in substantially the first position such that the projection means is inwardly biased and engages an engagement portion on the side edge of the surgical saw blade.

22. The connector assembly of claim 21, further comprising a collet being mounted within the tapered sleeve, the collet including a slot adapted to accommodate the surgical saw blade, wherein the slot is in alignment with the projection means of the gripper mechanism.

23. The connector assembly of claim of claim 17, further comprising means for outwardly biasing the projection means.

24. The connector assembly of claim 17, wherein the gripper mechanism includes an outer surface which corresponds to a slope of an inner taper of the tapered sleeve.

25. The connector assembly of claim 17, further comprising an end sleeve having a window corresponding to a position of the projection means, the projection means extending through the window when the projection means engages the engagement portion on the surgical saw blade.

26. The connector assembly of claim 17, wherein when the tapered sleeve extends from the housing in the second position, the sternum guard cannot be mounted on the end of the housing.

27. The connector assembly of claim 17, further comprising a clearance between the tapered sleeve and the sternum guard when the tapered sleeve is substantially in the second position and the sternum guard is mounted to the housing.

28. The connector assembly of claim 17, wherein the tapered sleeve is positioned substantially within the housing.

29. A surgical saw blade comprising:

a blade portion having a plurality of teeth;

an engagement portion extending from the blade portion to an end of the surgical saw blade, the engagement portion having opposing sloped surfaces extending substantially from the blade portion to the end of the saw blade, the opposing sloped surfaces extending outward from the blade portion to the end with relation to a lateral axis of the surgical saw blade; and substantially semi-rounded inner surfaces at an interface between the opposing sloped surfaces and the blade portion.

30. The surgical saw blade of claim 29, wherein the end of the surgical saw blade has a slope end of approximately 30 degrees.

* * * * *